US00PP21486P2

(12) United States Plant Patent
Misato

(10) Patent No.: US PP21,486 P2
(45) Date of Patent: Nov. 16, 2010

(54) ***VERBENA* PLANT NAMED 'SUNMARIMURA'**

(50) Latin Name: *Verbena hybrida*
Varietal Denomination: Sunmarimura

(75) Inventor: Tomoya Misato, Yamanashi (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/319,419

(22) Filed: Jan. 7, 2009

(51) Int. Cl.
*A01H 5/00* (2006.01)

(52) U.S. Cl. ..... Plt./308

(58) Field of Classification Search ..... Plt./308
See application file for complete search history.

(56) References Cited

U.S. PATENT DOCUMENTS

PP14,875 P2 * 6/2004 Sakazaki ..... Plt./308
PP16,165 P2 * 12/2005 Stemkens ..... Plt./308

OTHER PUBLICATIONS

Canadian Food Inspection Agency. Sunmarimura PBR 08-6182, 2009 [retrieved on Jan. 20, 2010]. Found on the Internet at:<http://www.inspection.gc.ca/english/plaveg/pbrpov/cropreport/ver/app00007171e.shtml> 3 pp.*
Canadian Food Inspection Agency Plant Varieties Journal Apr. 2008/No. 67, 2 pp.*

* cited by examiner

*Primary Examiner*—June Hwu
(74) *Attorney, Agent, or Firm*—C. A. Whealy

(57) ABSTRACT

A new and distinct cultivar of *Verbena* plant named 'Sunmarimura', characterized by its compact and trailing plant habit; vigorous growth habit; freely branching habit; early and freely flowering habit; long flowering period; and purple violet-colored flowers that are held above and beyond the foliage.

1 Drawing Sheet

Botanical designation: *Verbena hybrida.*
Cultivar denomination: 'Sunmarimura'.

BACKGROUND OF THE INVENTION

The present invention relates to a new and distinct cultivar of *Verbena* plant, botanically known as *Verbena hybrida*, and hereinafter referred to by the name 'Sunmarimura'.

The new *Verbena* plant is a product of a planned breeding program conducted by the Inventor in Higashiomi, Shiga, Japan. The objective of the breeding program is to create new compact, trailing and freely-branching *Verbena* cultivars with attractive flower coloration.

The new *Verbena* plant originated from a cross-pollination made by the Inventor in June, 2005 in Higashiomi, Shiga, Japan of a proprietary selection of *Verbena hybrida* identified as code number VW337, not patented, as the female, or seed, parent with a proprietary selection of *Verbena hybrida* identified as code number H-31, not patented, as the male, or pollen, parent. The new *Verbena* was discovered and selected by the Inventor as a single flowering plant within the progeny of the stated cross-pollination in a controlled greenhouse environment in Higashiomi, Shiga, Japan in October, 2005.

Asexual reproduction of the new *Verbena* plant by terminal cuttings in a controlled environment in Higashiomi, Shiga, Japan since November, 2005 has shown that the unique features of this new *Verbena* plant are stable and reproduced true to type in successive generations.

SUMMARY OF THE INVENTION

Plants of the new *Verbena* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunmarimura'. These characteristics in combination distinguish 'Sunmarimura' as a new and distinct cultivar of *Verbena:*

1. Compact and trailing plant habit.
2. Vigorous growth habit.
3. Freely branching habit.
4. Early and freely flowering habit.
5. Long flowering period.
6. Purple violet-colored flowers that are held above and beyond the foliage.

Plants of the new *Verbena* can be compared to plants of the female parent selection. Plants of the new *Verbena* differ primarily from plants of the female parent selection in the following characteristics:

1. Plants of the new *Verbena* are larger than plants of the female parent selection.
2. Plants of the new *Verbena* and the female parent selection differ in flower color as plants of the female parent selection have red purple-colored flowers.

Plants of the new *Verbena* can be compared to plants of the male parent selection. Plants of the new *Verbena* differ primarily from plants of the male parent selection in the following characteristics:

1. Plants of the new *Verbena* are larger than plants of the male parent selection.
2. Plants of the new *Verbena* have larger flowers than plants of the male parent selection.
3. Plants of the new *Verbena* and the male parent selection differ in flower color as plants of the male parent selection have pale violet-colored flowers.

Plants of the new *Verbena* can be compared to plants of *Verbena* 'Sunmariba', disclosed in U.S. Plant Pat. No. 10,801. In side-by-side comparisons conducted in Higashiomi, Shiga, Japan, plants of the new *Verbena* differed primarily from plants of 'Sunmariba' in the following characteristics:

1. Plants of the new *Verbena* were smaller than plants of 'Sunmariba'.
2. Plants of the new *Verbena* had smaller leaves than plants of 'Sunmariba'.
3. Plants of the new *Verbena* flowered earlier and more freely than plants of 'Sunmariba'.
4. Plants of the new *Verbena* had larger inflorescences and flowers than plants of 'Sunmariba'.
5. Plants of the new *Verbena* and 'Sunmariba' differed in flower color as plants of 'Sunmariba' had purple-colored flowers.

BRIEF DESCRIPTION OF THE PHOTOGRAPH

The accompanying colored photographs illustrate the overall appearance of the new *Verbena* plant, showing the colors as true as it is reasonably possible to obtain in colored reproductions of this type. Colors in the photographs may differ slightly from the color values cited in the detailed botanical description which accurately describe the colors of the new *Verbena*.

The photograph at the top of the sheet comprises a side perspective view of a typical flowering plant of 'Sunmarimura' grown in a container.

The photograph at the bottom of the sheet is a close-up view of a typical inflorescence of 'Sunmarimura'.

DETAILED BOTANICAL DESCRIPTION

The aforementioned photographs and following observations and measurements describe plants grown in 15-cm containers in Higashiomi, Shiga, Japan, under commercial practice during the summer in an outdoor nursery with day temperatures averaging 23° C. and night temperatures averaging 13° C. Plants had been growing for four and five months when the photographs and description, respectively, were taken. In the following description, color references are made to The Royal Horticultural Society Colour Chart, 2001 Edition, except where general terms of ordinary dictionary significance are used.

Botanical classification: *Verbena hybrida* 'Sunmarimura'.

Parentage:

*Female, or seed, parent.*—Proprietary selection of *Verbena hybrida* identified as code number VW337, not patented.

*Male, or pollen, parent.*—Proprietary seedling selection of *Verbena hybrida* identified as code number H-31, not patented.

Propagation:

*Type.*—By terminal cuttings.

*Time to initiate roots.*—About 10 to 14 days at 20° C. to 25° C.

*Time to produce a rooted young plant.*—About four weeks at 20° C. to 25° C.

*Root description.*—Fibrous; white, close to 158A, in color.

*Rooting habit.*—Freely branching.

Plant description:

*Plant and growth habit.*—Compact, trailing to decumbent growth habit; freely branching habit with numerous lateral branches developing per plant; pinching enhances lateral branch development; vigorous growth habit.

*Plant height.*—About 16.7 cm.

*Plant diameter.*—About 53.4 cm.

Lateral branch description:

*Length.*—About 25.2 cm.

*Diameter.*—About 2.6 mm.

*Internode length.*—About 2.9 cm.

*Strength.*—Strong.

*Texture.*—Pubescent.

*Color.*—Close to 146B.

Foliage description:

*Arrangement: Opposite, simple.*

*Length.*—About 2.9 cm.

*Width.*—About 1.8 cm.

*Shape.*—Narrowly ovate.

*Apex.*—Broadly acute.

*Base.*—Truncate.

*Margin.*—Serrate.

*Texture, upper and lower surfaces.*—Coarse; pubescent.

*Venation pattern.*—Pinnate; reticulate.

*Color.*—Developing and fully expanded leaves, upper surface: Close to 137A; venation, close to 137C. Developing and fully expanded leaves, lower surface: Close to 137C; venation, 144B.

*Petiole.*—Length: About 5.2 cm. Diameter: About 1.9 mm. Texture, upper and lower surfaces: Sparsely pubescent. Color, upper and lower surfaces: Close to 144B.

Flower description:

*Flower arrangement and habit.*—Salverform flowers arranged in hemispherical terminal racemes; flowers face mostly upright. Freely flowering habit with about 30 flowers per plant.

*Natural flowering season.*—Plants flower continuously from spring to late autumn in Japan; plants begin flowering about four weeks after planting.

*Flower longevity.*—Flowers last about one week on the plant; flowers not persistent.

*Fragrance.*—None detected.

*Inflorescence height.*—About 5.1 cm.

*Inflorescence diameter.*—About 6.2 cm.

*Flowers.*—Appearance: Flared trumpet, corolla fused, five-parted. Diameter: About 2 cm. Depth (height): About 3.1 cm. Tube length: About 2.2 cm. Tube diameter: About 1.4 mm.

*Flower buds.*—Length: About 1.7 cm. Diameter: About 3.4 mm. Shape: Clavate. Color: Close to N87A.

*Corolla.*—Arrangement: Single whorl of five fused petals. Petal length: About 8.9 mm. Petal width: About 7.7 mm. Petal lobe shape: Cordate. Petal lobe apex: Cordate. Petal margin: Entire. Petal texture, upper and lower surfaces: Smooth, glabrous. Color: Petal, when opening, upper surface: Close to N81A. Petal, when opening, lower surface: Close to 84A. Petal, fully opened, upper surface: Close to N81A; color becoming closer to N87A with development. Petal, fully opened, lower surface: Close to N87D, Throat: Close to 145C. Tube: Close to 145C.

*Calyx.*—Arrangement: One single narrow calyx tube per flower with five fused sepals. Sepal length: About 1.1 cm. Sepal width: About 1.1 mm. Sepal shape: Lanceolate. Sepal apex: Acute. Sepal margin: Entire.

Sepal texture, upper and lower surfaces: Smooth, glabrous. Sepal color, upper and lower surfaces: Close to 137C.

*Peduncles.*—Length: About 4.1 cm. Diameter: About 1.7 mm. Strength: Strong. Texture: Pubescent. Color: Close to 146B.

*Reproductive organs.*—Stamens: Quantity/arrangement: Four per flower, adnate to corolla tube. Stamen length: About 1.6 cm. Anther shape: Ellipsoidal. Anther size: About 1.2 mm by 0.9 mm. Anther color: Close to 144C. Pollen amount: Scarce. Pollen color: Yellow. Pistils: Quantity: One per flower. Pistil length: About 2.15 cm. Stigma shape: Bi-parted. Stigma color: Close to 144A. Style color: Close to 144D. Ovary color: Close to 146C. Fruits/seed: Fruit and seed development have not been observed.

Temperature tolerance: Plants of the new *Verbena* have been observed to tolerate temperatures from about 0° C. to about 35° C.

Pathogen/pest resistance: Plants of the new *Verbena* have not been observed to be resistant to pathogens and pests common to *Verbenas*.

It is claimed:

1. A new and distinct *Verbena* plant named 'Sunmarimura' as illustrated and described.

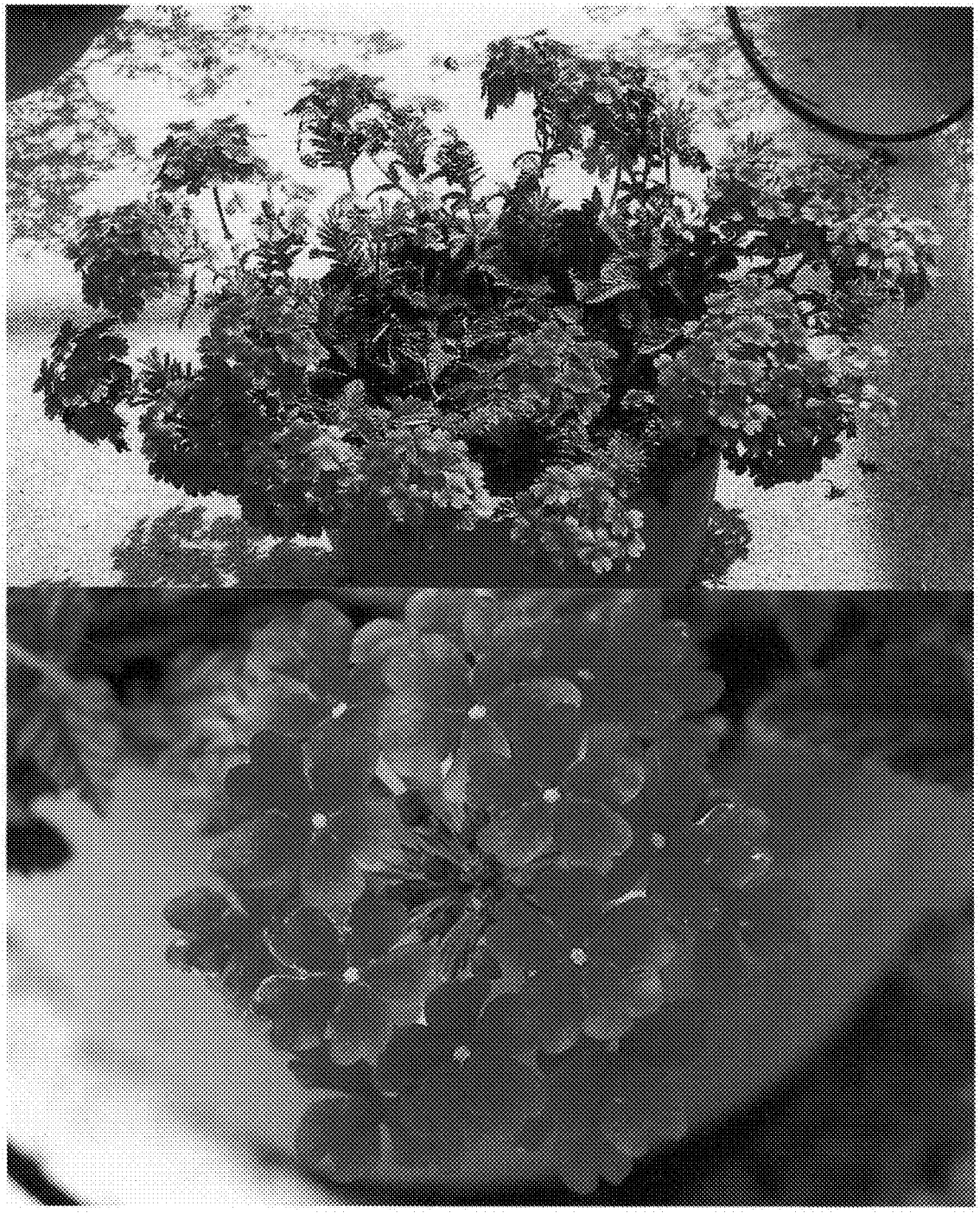

* * * * *